(12) United States Patent
Miyake et al.

(10) Patent No.: US 10,292,920 B2
(45) Date of Patent: May 21, 2019

(54) COMPOSITION FOR DYEING KERATIN FIBERS

(71) Applicant: L'OREAL, Paris (FR)

(72) Inventors: Shiho Miyake, Kawasaki (JP);
Hidetoshi Yamada, Kawasaki (JP);
Shoji Maruyama, Kawasaki (JP);
Daisuke Misu, Kawasaki (JP)

(73) Assignee: L'OREAL, Paris (FR)

( * ) Notice: Subject to any disclaimer, the term of this patent is extended or adjusted under 35 U.S.C. 154(b) by 193 days.

(21) Appl. No.: 15/315,512

(22) PCT Filed: May 29, 2015

(86) PCT No.: PCT/JP2015/066272
§ 371 (c)(1),
(2) Date: Jun. 20, 2017

(87) PCT Pub. No.: WO2015/186813
PCT Pub. Date: Dec. 10, 2015

(65) Prior Publication Data
US 2017/0209356 A1  Jul. 27, 2017

(30) Foreign Application Priority Data
Jun. 6, 2014 (JP) .................................. 2014-117413

(51) Int. Cl.
*A61Q 5/10* (2006.01)
*A61K 8/46* (2006.01)
*A61K 8/49* (2006.01)
*A61Q 5/06* (2006.01)

(52) U.S. Cl.
CPC ................ *A61K 8/46* (2013.01); *A61K 8/466* (2013.01); *A61K 8/494* (2013.01); *A61K 8/4986* (2013.01); *A61Q 5/065* (2013.01); *A61K 2800/4322* (2013.01)

(58) Field of Classification Search
CPC ...... A61K 8/4986; A61K 8/466; A61K 8/494; A61Q 5/065
See application file for complete search history.

(56) References Cited

U.S. PATENT DOCUMENTS

2002/0144356 A1  10/2002  Kawai et al.
2010/0229314 A1  9/2010   Takiguchi

FOREIGN PATENT DOCUMENTS

| DE | 102 00 185 A1 | 7/2002 | |
|----|---------------|--------|---|
| EP | 0 161 073 A2  | 11/1985 | |
| EP | 1 022 014 A1  | 7/2000 | |
| EP | 1 238 649 A2  | 9/2002 | |
| JP | 52015683 A *  | 2/1977 | ............... D06P 3/34 |
| JP | 2002-241245 A | 8/2002 | |
| JP | 2003-246715 A | 9/2003 | |
| JP | 2010-105998 A | 5/2010 | |
| JP | 2010-248123 A | 11/2010 | |
| JP | 2011-132192 A | 7/2011 | |
| WO | 2009/047916 A1 | 4/2009 | |

OTHER PUBLICATIONS

Engish absract (Aug. 23, 2018) of the Japanese Patent No. JP 52015683 A.*
International Search Report and Written Opinion for PCT/JP2015/066272, dated Aug. 7, 2015.
Office Action for counterpart Japanese Application No. 2014-117413, dated Dec. 10, 2018.

* cited by examiner

*Primary Examiner* — Eisa B Elhilo
(74) *Attorney, Agent, or Firm* — The Marbury Law Group, PLLC

(57) ABSTRACT

The present invention relates to a composition for dyeing keratin fibers, comprising (a) at least one direct dye; and (b) at least one sulfone compound represented by the following formula (I): wherein each of $R^1$ and $R^2$ independently denotes a monovalent $C_{1-30}$ aliphatic group or a monovalent $C_{6-30}$ aromatic group, which may optionally be substituted with at least one substituent; or $R^1$ and $R^2$, together with the sulfur atom which they are binding, form a 3-10 membered ring which may optionally be substituted with at least one substituent. The composition according to the present invention is a one-part composition and can prevent or reduce skin staining by the direct dye on the skin such as the scalp, while providing the keratin fibers with good cosmetic effects such as good coloring properties.

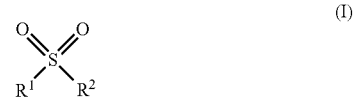

(I)

18 Claims, No Drawings

COMPOSITION FOR DYEING KERATIN FIBERS

CROSS REFERENCE TO RELATED APPLICATIONS

This is a national stage application of PCT/JP2015/066272, filed internationally on May 29, 2015, which claims priority to Japanese Application No. 2014-117413, filed on Jun. 6, 2014, both of which are incorporated by reference herein in their entireties.

TECHNICAL FIELD

The present invention relates to a composition for dyeing keratin fibers, in particular for dyeing keratin fibers with at least one direct dye, as well as a process using the same.

BACKGROUND ART

It is known to dye keratin fibers, in particular human hair, with dyeing compositions containing oxidative coloring precursors, generally called oxidative bases, such as ortho- or para-phenylenediamines, ortho- or para-aminophenols and heterocyclic compounds. These oxidative bases are generally combined with couplers. These bases and these couplers are colorless or weakly colored compounds which, combined with oxidizing products, can give rise to colored compounds through an oxidative condensation process.

This type of coloring by oxidation makes it possible to obtain colors with very high visibility, coverage of white hair and in a wide variety of shades but it results in damage to the keratin fibers by the use of oxidizing agents (in particular by repeated application or by combination with other hair treatments).

On the other hand, it is also known to dye keratin fibers, in particular human hair, with dyeing compositions containing direct dyes. Conventional direct dyes are in particular the following: benzene nitrates, anthraquinones, nitropyridines, azos, xanthines, acridines, azines, and triarylmethane type or natural colorings.

For example, JP-A-2002-241245 and WO 2009/047916 disclose a composition for dyeing hair, including a direct dye.

Hair coloration using direct dyes has advantages over hair coloration using oxidative dyes: it has no allergic issues, no damage to the hair, and it gives vivid color visibility.

DISCLOSURE OF INVENTION

However, skin staining has been an inevitable drawback of hair coloration using direct dyes.

In addition, in terms of usability, it is preferable that a composition for dyeing hair be a so-called one-part composition which is ready-to-use and therefore no mixing of two or more parts of the composition is necessary when coloring hair with the composition.

An objective of the present invention is to provide a composition for dyeing keratin fibers which uses a direct dye, but can prevent or reduce skin staining by the direct dye on the skin such as the scalp, while providing the keratin fibers with good cosmetic effects such as good coloring properties.

The above objective can be achieved by a composition for dyeing keratin fibers, comprising:

(a) at least one direct dye; and
(b) at least one sulfone compound represented by the following formula (I):

wherein
each of $R^1$ and $R^2$ independently denotes a monovalent $C_{1\text{-}30}$ aliphatic group or a monovalent $C_{6\text{-}30}$ aromatic group, which may optionally be substituted with at least one substituent; or $R^1$ and $R^2$, together with the sulfur atom which they are binding, form a 3-10 membered ring which may optionally be substituted with at least one substituent.

The (a) direct dye may be selected from the group consisting of acidic direct dyes, basic direct dyes and neutral direct dyes, and preferably from acidic direct dyes.

The amount of the (a) direct dye in the composition according to the present invention may range from 0.001% to 5% by weight, preferably from 0.01% to 3% by weight, and more preferably from 0.05% to 2% by weight, relative to the total weight of the composition.

In the above formula (I), the monovalent $C_{1\text{-}30}$ aliphatic group may be a saturated monovalent $C_{1\text{-}30}$ aliphatic hydrocarbon group, preferably a linear or branched $C_{1\text{-}30}$ alkyl group, or a $C_{3\text{-}30}$ cycloalkyl group, or an unsaturated monovalent $C_{2\text{-}30}$ aliphatic hydrocarbon group.

In the above formula (I), the monovalent $C_{6\text{-}30}$ aromatic group may be a monovalent $C_{6\text{-}30}$ aromatic hydrocarbon group. The monovalent $C_{6\text{-}30}$ aromatic hydrocarbon group may be a $C_{6\text{-}30}$ aryl group, or a linear or branched $C_{7\text{-}30}$ aralkyl group.

In the above formula (I), $R^1$ and $R^2$, together with the sulfur atom which they are binding, may form a 3-10 membered aliphatic ring which may optionally be substituted with at least one substituent.

The amount of the (b) sulfone compound in the composition according to the present invention may range from 0.5 to 30% by weight, preferably from 1 to 20% by weight, and more preferably from 2 to 10% by weight, relative to the total weight of the composition.

The composition according to the present invention may further comprise water.

The pH of the composition according to the present invention may range from 2 to 7, preferably from 2 to 6 and more preferably from 2 to 4.

The composition according to the present invention may further comprise (c) at least one buffering agent, preferably an amino acid, amino acid derivative, or a combination of an organic acid or inorganic acid and a salt thereof.

The amount of the (c) buffering agent in the composition according to the present invention may range from 0.1 to 15% by weight, preferably from 0.5 to 10% by weight, and more preferably from 0.5 to 5% by weight, relative to the total weight of the composition.

The composition according to the present invention may further comprise (d) at least one organic solvent.

The amount of the (d) organic solvent in the composition according to the present invention may range from 1 to 35% by weight, preferably from 5 to 25% by weight, and more preferably from 10 to 15% by weight, relative to the total weight of the composition.

The present invention also relates to a process for dyeing keratin fibers, comprising the step of applying the composition according to the present invention to the keratin fibers.

BEST MODE FOR CARRYING OUT THE INVENTION

After diligent research, the inventors have discovered that it is possible to provide a composition, preferably a one-part composition, for dyeing keratin fibers which includes a direct dye, but can prevent or reduce skin staining by the direct dye on the skin such as the scalp, while providing the keratin fibers with good cosmetic effects such as good coloring properties.

Thus, the composition according to the present invention is intended for dyeing keratin fibers and comprises:
(a) at least one direct dye; and
(b) at least one sulfone compound represented by the following formula (I):

wherein
each of $R^1$ and $R^2$ independently denotes a monovalent $C_{1-30}$ aliphatic group or a monovalent $C_{6-30}$ aromatic group, which may optionally be substituted with at least one substituent; or
$R^1$ and $R^2$, together with the sulfur atom which they are binding, form a 3-10 membered ring which may optionally be substituted with at least one substituent.

The composition according to the present invention is preferably a so-called one-part composition which is ready-to-use and therefore no mixing of two or more parts of the composition is necessary when coloring hair with the composition.

Hereafter, the composition according to the present invention will be described in a detailed manner.

[Direct Dye]

The composition according to the present invention includes (a) at least one direct dye. Two or more direct dyes may be used in combination. Thus, a single type of direct dye or a combination of different types of direct dyes may be used.

A direct dye means a colored substance which does not require the use of an oxidizing agent in order to develop its color.

The direct dye may be a natural direct dye or a synthetic direct dye.

The expression "natural direct dye" is understood to mean any dye or dye precursor that is naturally occurring and is produced by extraction (and optionally purification) from a plant matrix or an animal such as an insect, optionally in the presence of natural compounds such as ash or ammonia.

As natural direct dyes, mention may be made of quinone dyes (such as lawsone and juglone), alizarin, purpurin, laccaic acid, carminic acid, kermesic acid, purpurogallin, protocatechaldehyde, indigoids such as indigo, sorghum, isatin, betanin, curcuminoids (such as curcumin), spinulosin, various types of chlorophyll and chlorophyllin, hematoxylin, hematein, brazilein, brazilin, safflower dyes (such as carthamin), flavonoids (such as rutin, quercetin, catechin, epicatechin, morin, apigenidin, and sandalwood), anthocyans (such as apigeninidin and apigenin), carotenoids, tannins, orceins, santalins and cochineal carmine.

It is also possible to use extracts or decoctions containing natural direct dye(s), in particular henna-based extracts, *curcuma longa* extract, sorghum leaf-sheath extract, haematoxylon campechianum extract, green tea extract, pine bark extract, cocoa extract, and logwood extract.

It is preferable that the natural direct dye be chosen from the group consisting of curcuminoids, santalins, chlorophyllin, haematoxylin, haematein, brazilein, brazilin, sorghum, laccaic acid, lawsone, juglone, alizarin, purpurin, carminic acid, kermesic acid, purpurogallin, protocatechaldehyde, indigoids, isatin, spinulosin, apigenin, orcein, betanin, flavonoids, anthocyans, and extracts or decoctions containing these compounds.

Alternatively, the natural direct dyes may be preferably chosen, for example, from hydroxylated quinones, indigoids, hydroxyflavones, santalins A and B, isatin and its derivatives, and brasilin and its hydroxylated derivative.

The hydroxylated quinones are preferably benzoquinones, naphthoquinones, and mono- or polyhydroxylated anthraquinones which are optionally substituted with groups such as alkyl, alkoxy, alkenyl, chloro, phenyl, hydroxyalkyl and carboxyl.

The naphthoquinones are preferably lawsone, juglone, flaviolin, naphthazarin, naphthopurpurin, lapachol, plumbagin, chloroplumbagin, droserone, shikonin, 2-hydroxy-3-methyl-1,4-naphthoquinone, 3,5-dihydroxy-1,4-naphthoquinone, 2,5-dihydroxy-1,4-naphthoquinone, 2-methoxy-5-hydroxy-1,4-naphthoquinone and 3-methoxy-5-hydroxy-1,4-naphthoquinone.

The benzoquinones are preferably spinulosin, atromentin, aurentioglyocladin, 2,5-dihydroxy-6-methylbenzoquinone, 2-hydroxy-3-methyl-6-methoxybenzoquinone, 2,5-dihydroxy-3,6-diphenylbenzoquinone, 2,3-dimethyl-5-hydroxy-6-methoxybenzoquinone and 2,5-dihydroxy-6-isopropylbenzoquinone.

The anthraquinones are preferably alizarin, quinizarin, purpurin, carminic acid, chrysophanol, kermesic acid, rhein, aloe emodin, pseudopurpurin, quinizarincarboxylic acid, frangula emodin, 2-methylquinizarin, 1-hydroxyanthraquinone and 2-hydroxyanthraquinone.

The indigoids are preferably indigo, indirubin, isoindigo and Tyrian purple.

The hydroxyflavones are preferably quercetin and morin.

The expression "synthetic direct dye" is understood to mean any dye or dye precursor that is produced by chemical synthesis.

The direct dye can be selected from the group consisting of acidic (anionic) direct dyes, basic. (cationic) direct dyes, and neutral (nonionic) direct dyes.

Non-limiting examples of syntheticdyes include (nonionic) neutral, anionic (acidic), and cationic (basic) dyes such as azo, methine, carbonyl, azine, nitro(hetero)aryl types or tri(hetero)arylmethane direct dyes, porphyrins and phthalocyanines, alone or as mixtures.

More particularly, the azo dyes comprise an —N=N— functional group, the two nitrogen atoms of which are not simultaneously involved in a ring. However, it is not ruled out for one of the two nitrogen atoms of the —N=N— sequence to be involved in a ring.

The dyes of the family of the methines are more particularly compounds comprising at least one sequence chosen from >C=C< and —N=C<, the two atoms of which are not simultaneously involved in a ring. However, it is specified that one of the nitrogen or carbon atoms of the sequences can be involved in a ring. More particularly, the dyes of this family result from compounds of the following types: true methine (comprising one or more of the above-mentioned —C=C— sequences); azomethine (comprising at least one or more —C=N— sequences) with, for example, the azacarbocyanines and their isomers, the diazacarbocyanines and their isomers, the tetraazacarbocyanines; mono- and diarylmethane; indoamines (or diphenylamines); indophenols; indoanilines.

As regards the dyes of the family of the carbonyls, mention may be made, for example, of synthetic dyes chosen from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, naphthalimide, anthrapyrimidine, diketopyrrolopyrrole or coumarin dyes.

As regards the dyes of the family of the cyclic azines, mention may in particular be made of azine, xanthene, thioxanthene, fluorindine, acridine, (di)oxazine, (di)thiazine or pyronin dyes.

The nitro(hetero)aromatic dyes are more particularly nitrobenzene or nitropyridine direct dyes.

As regards the dyes of porphyrin or phthalocyanine type, use may be made of cationic or noncationic compounds optionally comprising one or more metals or metal ions, such as, for example, alkali and alkaline earth metals, zinc and silicon.

Mention may be made, as examples of synthetic direct dyes which are particularly suitable, of nitrobenzene dyes, azo, azomethine or methine direct dyes, azacarbocyanines, such as tetraazacarbocyanines (tetraazapentamethines), quinone and in particular anthraquinone, naphthoquinone or benzoquinone direct dyes, or azine, xanthene, triarylmethane, indoamine, phthalocyanine and porphyrin direct dyes, alone or as mixtures. More preferably still, these synthetic direct dyes are chosen from nitrobenzene dyes, azo, azomethine or methine direct dyes and tetraazacarbocyanines (tetraazapentamethines); alone or as mixtures.

Mention may be made, among the azo, azomethine, methine or tetraazapentamethine direct dyes which can be used according to the invention, of the cationic dyes described in Patent Applications WO 95/15144, WO 95/01772 and EP 714 954; FR 2 189 006, FR 2 285 851, FR-2 140 205, EP 1 378 544 and EP 1 674 073.

Thus, mention may very particularly be made of the cationic direct dyes corresponding to the following formulae:

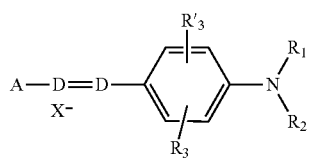

in which:

D represents a nitrogen atom or the —CH group, $R_1$ and $R_2$, which are identical or different, represent a hydrogen atom; a $C_1$-$C_4$ alkyl radical which can be substituted by a —CN, —OH or —NH$_2$ radical or can form, with a carbon atom of the benzene ring, an optionally oxygen-comprising or nitrogen-comprising heterocycle which can be substituted by one or more $C_1$-$C_4$ alkyl radicals; or a 4'-aminophenyl radical, $R_3$ and $R'_3$, which are identical or different, represent a hydrogen atom, a halogen atom chosen from chlorine, bromine, iodine and fluorine, a cyano radical, a $C_1$-$C_4$ alkyl radical, a $C_1$-$C_4$ alkoxy radical or an acetyloxy radical, $X^-$ represents an anion, preferably chosen from chloride, methyl sulphate and acetate, A represents a group chosen from the following structures:

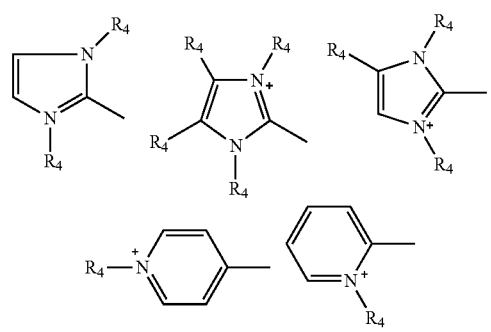

in which $R_4$ represents a $C_1$-$C_4$ alkyl radical which can be substituted by a hydroxyl radical;

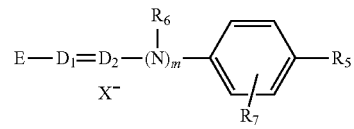

in which:

$R_5$ represents a hydrogen atom, a $C_1$-$C_4$ alkoxy radical or a halogen atom, such as bromine, chlorine, iodine or fluorine, $R_6$ represents a hydrogen atom or a $C_1$-$C_4$ alkyl radical or forms, with a carbon atom in the benzene ring, a heterocycle which optionally comprises oxygen and/or is optionally substituted by one or more $C_1$-$C_4$ alkyl groups, $R_7$ represents a hydrogen atom or a halogen atom, such as bromine, chlorine, iodine or fluorine, $D_1$ and $D_2$, which are identical or different, represent a nitrogen atom or the —CH group, m=0 or 1, $X^-$ represents a cosmetically acceptable anion preferably chosen from chloride, methyl sulphate and acetate, E represents a group chosen from the following structures:

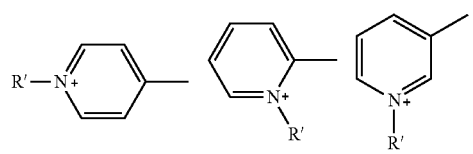

in which R' represents a $C_1$-$C_4$ alkyl radical;

when m=0 and when $D_1$ represents a nitrogen atom, then E can also denote a group with the following structure:

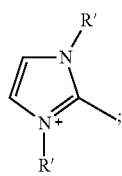

in which R' represents a $C_1$-$C_4$ alkyl radical.

The synthetic direct dye may be selected from fluorescent dyes. Two or more types of fluorescent dyes may be used in combination.

The use of some fluorescent dyes may make it possible to obtain, on dark hair, colors which are more visible than with conventional hydrophilic or hydrophobic direct dyes.

Furthermore, these fluorescent dyes, when applied to dark hair, may also make it possible to lighten the hair without damaging it.

As used herein, the term "fluorescent dyes" is understood to mean fluorescent compounds and optical brighteners. In at least one embodiment, the fluorescent dye is soluble in the medium of the composition.

Fluorescent dyes are fluorescent compounds which absorb visible radiation, for example, wavelengths ranging from 400 to 800 nm, and which are capable of re-emitting light in the visible region at a higher wavelength.

According to one embodiment, the fluorescent dyes useful for the present invention re-emit orange-colored fluorescent light. They exhibit, for instance, a maximum re-emission wavelength ranging from 500 to 700 nm.

Non-limiting examples of fluorescent dyes include compounds known in the art, for example, those described in Ullmann's Encyclopedia of Industrial Chemistry, Release 2004, 7th edition, "Fluorescent Dyes" chapter.

The optical brighteners of the present disclosure, also known under the name of "brighteners", or "fluorescent brighteners", or "fluorescent brightening agents" or "FWA", or "fluorescent whitening agents", or "whiteners", or "fluorescent whiteners", are colorless transparent compounds as they do not absorb in visible light but only in ultraviolet light (wavelengths ranging from 200 to 400 nanometers) and convert the energy absorbed into fluorescent light of higher wavelength emitted in the visible part of the spectrum, generally in the blue and/or green, that is to say in wavelengths ranging from 400 to 550 nanometers.

Optical brighteners are known in the art, for example, they are described in Ullmann's Encyclopedia of Industrial Chemistry (2002), "Optical Brighteners" and Kirk-Othmer Encyclopedia of Chemical Technology (1995): "Fluorescent Whitening Agents".

The fluorescent dyes which can be used in the composition of the present disclosure include compounds known from the art, for example, those described in French Patent No. 2 830 189.

Soluble fluorescent compounds that may especially be mentioned include those belonging to the following families: naphthalimides, coumarins, xanthenes and in particular xanthenodiquinolizines and azaxanthenes; naphtholactams; azlactones; oxazines; thiazines; dioxazines; azo compounds; azomethines; methines; pyrazines; stilbenes; ketopyrroles; and pyrenes.

If present, the fluorescent dyes are preferred, more particularly, those re-emitting orange-colored fluorescent light.

In terms of ionic nature, the (a) direct dye may be selected from the group consisting of acidic direct dyes, basic direct dyes and neutral direct dyes, which covers all possible types of direct dyes, such as so-called nitro dyes and HC dyes. Acidic direct dyes have an anionic moiety in their chemical structure. Basic direct dyes have a cationic moiety in their chemical structure. Neutral direct dyes are nonionic.

According to an embodiment, it is preferable that the (a) direct dye be selected from acidic direct dyes.

The anionic direct dyes are commonly known as "acidic direct dyes" for their affinity with alkaline substances (see, for example, "Industrial Dyes, Chemistry, Properties, Application", Klaus Hunger Ed. Wiley-VCH Verlag GmbH & Co KGaA, Weinheim 2003). Anionic or acid dyes are known in the literature (see, for example, "Ullman's Encyclopedia of Industrial Chemistry", Azo Dyes, 2005 Wiley-VCH Verlag GmbH & Co. KGaA, Weinheim 10.1002/14356007.a03 245, point 3.2; ibid, Textile Auxiliaries, 2002 Wiley-VCH Verlag GmbH & Co. KGaA, Weinheim 10.1002/14356007. a26 227 and "Ashford's Dictionary of Industrial Chemicals", Second Edition, p. 14-p. 39, 2001).

The term "anionic direct dyes" means any direct dye comprising in its structure at least one sulfonate group $SO_3^-$ and/or at least one carboxylate group $C(O)O^-$ and/or at least one phosphonate group $P(=O)O^-O^-$ and optionally one or more anionic groups $G^-$ with $G^-$, which may be identical or different, representing an anionic group chosen from alkoxide $O^-$, thioalkoxide $S^-$, phosphonate, carboxylate and thiocarboxylate: $C(Q)Q'^-$ with Q and Q', which may be identical or different, representing an oxygen or sulfur atom; preferably, $G^-$ represents a carboxylate, i.e. Q and Q' represent an oxygen atom.

The preferred anionic dyes of formula of the invention are chosen from acidic nitro direct dyes, acidic azo dyes, acidic azine dyes, acidic triarylmethane dyes, acidic indoamine dyes, acidic anthraquinone dyes, anionic styryl dyes, and indigoids and acidic natural dyes; each of these dyes containing at least one sulfonate, phosphonate or carboxylate group bearing a cationic counterion $X^+$, where $X^+$ represents an organic or mineral cationic counter ion preferably chosen from alkali and alkaline-earth metals, such as $Na^+$ and $K^+$ Preferred acid dyes may be chosen from:

a) The Diaryl Anionic Azo Dyes of Formula (II) or (II'):

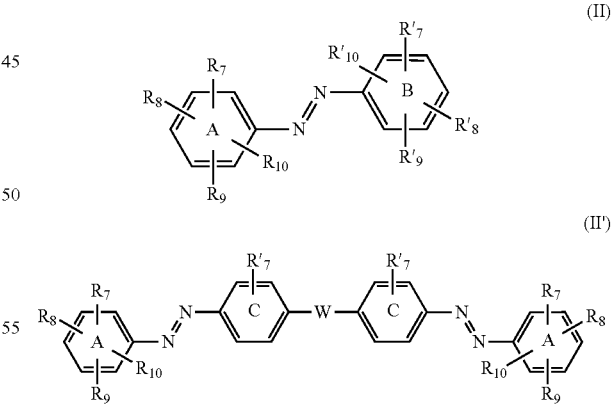

in which formulae (II) and (II'):

$R_7$, $R_8$, $R_9$, $R_{10}$, $R'_7$, $R'_8$, $R'_9$ and $R'_{10}$, which may be identical or different, represent a hydrogen atom or a group chosen from:
alkyl;
alkoxy, alkylthio;
hydroxyl, mercapto;
nitro;

R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;

(O)$_2$S(O$^-$)—, X$^+$ as defined previously;

(O)CO$^-$—, X$^+$ as defined previously;

(O)P(O$_2$$^-$)—, 2X$^+$ as defined previously;

R"—S(O)$_2$—, with R" representing a hydrogen atom or an alkyl, aryl, (di)(alkyl)amino or aryl(alkyl)amino group; preferably a phenylamino or phenyl group;

R'"—S(O)$_2$—X'— with R'" representing an alkyl or optionally substituted aryl group, X' as defined previously;

(di)(alkyl)amino;

aryl(alkyl)amino optionally substituted with one or more groups chosen from i) nitro; ii) nitroso; iii) (O)$_2$S(O$^-$)—, X$^+$ and iv) alkoxy with X$^+$;

optionally substituted heteroaryl; preferably a benzothiazolyl group;

cycloalkyl; especially cyclohexyl,

Ar—N=N— with Ar representing an optionally substituted aryl group, preferably a phenyl optionally substituted with one or more alkyl, (O)$_2$S(O$^-$)—, X$^+$ or phenylamino groups;

or alternatively two contiguous groups R$_7$ with R$_8$ or R$_8$ with R$_9$ or R$_9$ with R$_{10}$ together form a fused benzo group A'; and R'$_7$ with R'$_8$ or R'$_8$ with R'$_9$ or R'$_9$ with R'$_{10}$ together form a fused benzo group B'; with A' and B' optionally substituted with one or more groups chosen from i) nitro; ii) nitroso; iii) (O)$_2$S(O$^-$)—, X$^+$; iv) hydroxyl; v) mercapto; vi) (di)(alkyl)amino; vii) R°—C(X)—X'—; viii) R°—X'—C(X)—; ix) R°—X'—C(X)—X"—; x) Ar—N=N— and xi) optionally substituted aryl(alkyl)amino; with X$^+$, R°, X, X', X" and Ar as defined previously;

W represents a sigma bond σ, an oxygen or sulfur atom, or a divalent radical i) —NR— with R as defined previously, or ii) methylene —C(R$_a$)(R$_b$)— with R$_a$ and R$_b$, which may be identical or different, representing a hydrogen atom or an aryl group, or alternatively R$_a$ and R$_b$ form, together with the carbon atom that bears them, a Spiro cycloalkyl; preferably W represents a sulfur atom or R$_a$ and R$_b$ together form a cyclohexyl;

it being understood that formulae (II) and (II') comprise at least one sulfonate (O)$_2$S(O$^-$)—, X$^+$ or phosphonate (O)P(O$_2$$^-$) 2X$^+$ or carboxylate (O)C(O$^-$)—, X$^+$ radical on one of the rings A, A', B, B' or C with X$^+$ as defined previously;

As examples of dyes of formula (II), mention may be made of Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Food Red 17, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3; Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Pigment Red 57;

and as examples of dyes of formula (II'), mention may be made of Acid Red 111, Acid Red 134, Acid yellow 38;

b) The Anthraquinone Dyes of Formulae (III) and (III'):

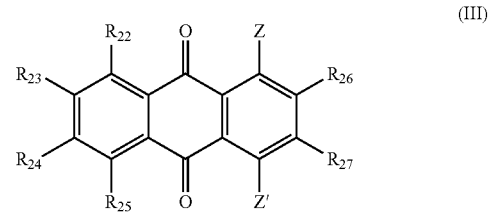

(III)

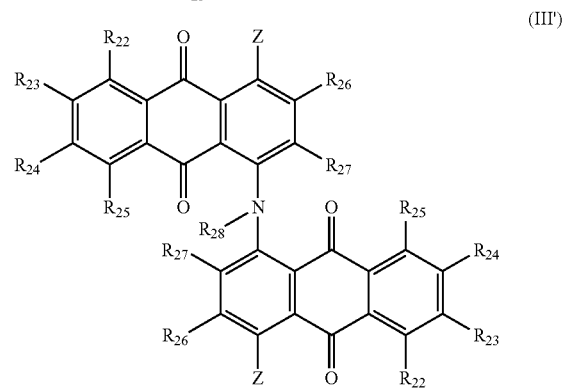

(III')

in which formulae (III) and (III'):

R$_{22}$, R$_{23}$, R$_{24}$, R$_{25}$, R$_{26}$ and R$_{27}$, which may be identical or different, represent a hydrogen or halogen atom or a group chosen from:

alkyl;

hydroxyl, mercapto;

alkoxy, alkylthio;

aryloxy or arylthio optionally substituted, preferably substituted with one or more groups chosen from alkyl and (O)$_2$S(O$^-$)—, X$^+$ with X$^+$ as defined previously;

aryl(alkyl)amino optionally substituted with one or more groups chosen from alkyl and (O)$_2$S(O$^-$)—, X$^+$ with X$^+$ as defined previously;

(di)(alkyl)amino;

(di)(hydroxyalkyl)amino;

(O)$_2$S(O$^-$)—, X$^+$ with X$^+$ as defined previously;

Z' represents a hydrogen atom or a group NR$_{28}$R$_{29}$ with R$_{28}$ and R$_{29}$, which may be identical or different, representing a hydrogen atom or a group chosen from:

alkyl;

polyhydroxyalkyl such as hydroxyethyl;

aryl optionally substituted with one or more groups, particularly i) alkyl such as methyl, n-dodecyl, n-butyl; ii) (O)$_2$S(O$^-$)—, X$^+$ with X$^+$ as defined previously; iii) R°—C(X)—X'—, R°—X'—C(X)—, R°—X'—C(X)—X"— with R°, X, X' and X" as defined previously, preferably R° represents an alkyl group;

cycloakyl; especially cyclohexyl;

—Z represents a group chosen from hydroxyl and NR'$_{28}$R'$_{29}$ with R'$_{28}$ and R'$_{29}$, which may be identical or different, representing the same atoms or groups as R$_{28}$ and R$_{29}$ as defined previously;

it being understood that formulae (III) and (III') comprise at least one sulfonate group (O)$_2$S(O$^-$)—, X$^+$ with X$^+$ as defined previously;

As examples of dyes of formula (III), mention may be made of Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; EXT Violet 2, and as examples of dyes of formula (III'), mention may be made of Acid Black 48; and g) The Quinoline-Based Dyes of Formula (IV):

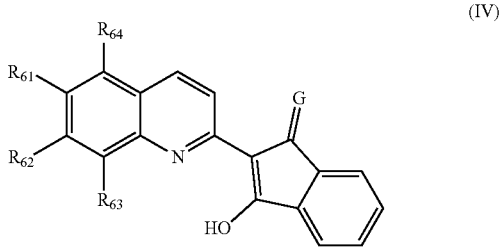

(IV)

in which formula (IV):
R$_{61}$ represents a hydrogen or halogen atom or an alkyl group;
R$_{62}$, R$_{63}$ and R$_{64}$, which may be identical or different, represent a hydrogen atom or a group (O)$_2$S(O$^-$)—, X$^+$ with X$^+$ as defined previously;
or alternatively R$_{61}$ with R$_{62}$, or R$_{61}$ with R$_{64}$, together form a benzo group optionally substituted with one or more groups (O)$_2$S(O$^-$)—, X$^+$ with X$^+$ as defined previously;
G represents an oxygen or sulfur atom or a group NR$_e$ with R$_e$ representing a hydrogen atom or an alkyl group; particularly G represents an oxygen atom;
it being understood that formula (IV) comprises at least one sulfonate group (O)$_2$S(O$^-$)—, X$^+$ with X$^+$ as defined previously;

As examples of dyes of formula (IV), mention may be made of Acid Yellow 2, Acid Yellow 3 and Acid Yellow 5.

It is preferable that the acidic direct dye be selected from the group consisting of Yellow 5, Orange 4, EXT. Violet 2 and Acid Black 1.

The composition according to the present invention may contain the (a) direct dye(s) in an amount of from 0.001% to 5% by weight, preferably from 0.01 to 3% by weight, and more preferably 0.05 to 2% by weight, relative to the total weight of the composition.

[Sulfone Compound]

The composition according to the present invention includes (b) at least one specific sulfone compound. Two or more specific sulfone compounds may be used in combination. Thus, a single type of specific sulfone compound or a combination of different types of sulfone compounds may be used.

The (b) sulfone compound used in the present invention can be represented by the following formula (I):

(I)

wherein
each of R$^1$ and R$^2$ independently denotes a monovalent C$_{1-30}$, preferably C$_{1-20}$, more preferably C$_{1-10}$ aliphatic group or a monovalent C$_{6-30}$, preferably C$_{6-20}$, more preferably C$_{6-10}$ aromatic group, which may optionally be substituted with at least one substituent; or R$^1$ and R$^2$, together with the sulfur atom which they are binding, form a 3-10, preferably 4-10, and more preferably 4-8 membered ring which may optionally be substituted with at least one substituent.

In the above formula (I), the monovalent C$_{1-30}$, preferably C$_{1-20}$, and more preferably C$_{1-10}$ aliphatic group may be
a saturated monovalent C$_{1-30}$, preferably C$_{1-20}$, and more preferably C$_{1-10}$ aliphatic hydrocarbon group, preferably a linear or branched C$_{1-30}$, preferably C$_{1-20}$, and more preferably C$_{1-10}$ alkyl group, or a C$_{3-30}$, preferably C$_{4-20}$, and more preferably C$_{5-10}$ cycloalkyl group, or
an unsaturated monovalent C$_{2-30}$, preferably C$_{2-20}$, and more preferably C$_{2-10}$ aliphatic hydrocarbon group.

As examples of a linear or branched C$_{1-30}$, preferably C$_{1-20}$, and more preferably C$_{1-10}$ alkyl group, mention may be made of a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, and the like.

As examples of a C$_{3-30}$, preferably C$_{4-20}$, and more preferably C$_{5-10}$ cycloalkyl group, mention may be made of a cyclopropyl group, a cyclobutyl group, a cyclopentyl group, a cyclohexyl group, a cycloheptyl group, a cyclooctyl group, and the like.

As examples of an unsaturated monovalent C$_{2-30}$, preferably C$_{2-20}$, and more preferably C$_{2-10}$ aliphatic hydrocarbon group, mention may be made of a linear or branched C$_{2-30}$, preferably C$_{2-20}$, and more preferably C$_{2-10}$ alkenyl group such as a vinyl group, a 1-propenyl group, an allyl group, an isopropenyl group, a 1-butenyl group, a 2-butenyl group, a pentenyl group, a hexenyl group, and the like; as well as, a C$_{2-30}$, preferably C$_{2-20}$, and more preferably C$_{2-10}$ cycloalkenyl group such as a cyclopentenyl group, a cyclohexenyl group, and the like.

In the above formula (I), the monovalent C$_{6-30}$, preferably C$_{6-20}$, and more preferably C$_{6-10}$ aromatic group may be a monovalent C$_{6-30}$, preferably C$_{6-20}$, and more preferably C$_{6-10}$ aromatic hydrocarbon group. The term "aromatic group" here means a group including at least one aromatic moiety. Thus, the monovalent C$_{6-30}$, preferably C$_{6-20}$, and more preferably C$_{6-10}$ aromatic group may be a C$_{6-30}$, preferably C$_{6-20}$, and more preferably C$_{6-10}$ aryl group, or a linear or branched C$_{7-30}$, preferably C$_{7-20}$, and more preferably C$_{7-10}$ aralkyl group.

As examples of a C$_{6-30}$, preferably C$_{6-20}$, and more preferably C$_{6-10}$ aryl group, mention may be made of a phenyl group, a tolyl group, a xylyl group, a mesityl group, and the like.

As examples of a linear or branched C$_{7-30}$, preferably C$_{7-20}$, and more preferably C$_{7-10}$ aralkyl group, mention may be made of a benzyl group, a phenethyl group and the like.

In the above formula (I), R$^1$ and R$^2$, together with the sulfur atom which they are binding, may form a 3-10, preferably 4-10, and more preferably 4-8 membered aliphatic ring which may optionally be substituted with at least one substituent.

The 3-10, preferably 4-10, and more preferably 4-8 membered aliphatic ring may be formed by a C$_{3-10}$, preferably C$_{4-10}$, and more preferably C$_{4-8}$ divalent, linear or branched, saturated or unsaturated hydrocarbon group, which binds to the sulfur atom.

As examples of a C$_{3-10}$, preferably C$_{4-10}$, and more preferably C$_{4-8}$ divalent, linear or branched, saturated hydrocarbon group, mention may be made of a C$_{3-10}$, preferably C$_{4-10}$, and more preferably C$_{4-8}$ alkylene group such as a propylene group, an isopropylene (—CH$_2$—CH(CH$_3$)—)

group, an n-butylene group, an isobutylene (—CH$_2$—CH(CH$_3$)—CH$_2$—) group, a sec-butylene (—CH(CH$_3$)—CH$_2$—CH$_2$—) group, a tert-butylene (—CH$_2$—C(CH$_3$)$_2$—) group, a pentylene group, a hexylene group, and the like.

As examples of a C$_{3-10}$, preferably C$_{4-10}$, and more preferably C$_{4-8}$ divalent, linear or branched, unsaturated hydrocarbon group, mention may be made of a C$_{3-10}$, preferably C$_{4-10}$, and more preferably C$_{4-8}$ alkenylene group such as a propenylene group, 1-butenylene, 2-butenylene group and the like.

As examples of the substituent which may be present on the monovalent C$_{1-30}$, preferably C$_{1-20}$, and more preferably C$_{140}$ aliphatic or a monovalent C$_{6-30}$, preferably C$_{6-20}$, and more preferably C$_{6-10}$ aromatic group, as R$^1$ or R$^2$, or on the 3-10, preferably 4-10, and more preferably 4-8 membered ring formed by R$^1$ and R$^2$ together with the sulfur atom which they are binding, mention may be made of a monovalent functional group such as a halogen atom, a hydroxyl group, a C$_1$-C$_6$ alkoxy group, an amino group, a C$_1$-C$_6$ alkylamino group, a C$_1$-C$_6$ dialkylamino group, a nitro group, a carbonyl group, an acyl group, a carboxyl group, a cyano group and the like.

The monovalent C$_{1-30}$, preferably C$_{1-20}$, and more preferably C$_{1-10}$ aliphatic or a monovalent C$_{6-30}$, preferably C$_{6-20}$, and more preferably C$_{6-10}$ aromatic group, as R$^1$ or R$^2$, or the 3-10, preferably 4-10, and more preferably 4-8 membered ring formed by R$^1$ and R$^2$ together with the sulfur atom which they are binding, may optionally contain at least one heteroatom selected from the group consisting of an oxygen, nitrogen and sulfur atom, in the above substituent or in the main hydrocarbon chain of the group or the ring.

As specific examples of the (b) sulfone compound used in the present invention, mention may be made of dimethyl sulfone, methyl ethyl sulfone, diethyl sulfone, methyl isopropyl sulfone, ethyl isopropyl sulfone, diisopropylsulfone, 2-chloroethyl ethyl sulfone, di-n-butylsulfone, divinylsulfone; diphenyl sulfone, bis(4-hydroxyphenyl)sulfone, bis(4-aminophenyl)sulfone, bis(3-aminophenylsulfone), bis(4-chlorophenylsulfone), bis(4-fluorophenyl)sulfone, 2-hydroxyphenyl-4-hydroxyphenyl sulfone, phenyl-4-chlorophenyl sulfone, phenyl-2-aminophenyl sulfone, bis(3-amino-4-hydroxyphenyl)sulfone, dibenzylsulfone; sulforane, 3-sulforene; and the like.

It is preferable that the (b) sulfone compound be in the form of a liquid at temperature ranging from 0 to 70° C., preferably from 10 to 50° C., more preferably from 20 to 40° C., and even more preferably at room temperature (25° C.).

Since the composition according to the present invention includes the (b) sulfone compound(s), it can prevent or reduce skin staining by the (a) direct dye(s) on the skin such as the scalp.

The amount of the (b) sulfone compound(s) in the composition according to the present invention may range from 0.5 to 30% by weight, preferably from 1 to 20% by weight, and more preferably from 2 to 10% by weight, relative to the total weight of the composition.

[Water]

The composition according to the present invention may further comprise water.

The amount of water in the composition according to the present invention may range from 10% to 90% by weight, preferably from 20% to 85% by weight, and more preferably from 30 to 80% by weight, relative to the total weight of the composition. The pH of the composition according to the present invention in this case may range from 2 to 7, preferably from 2 to 6 and more preferably from 2 to 4.

[Buffering Agent]

It is preferable that the composition according to the present invention further comprise (c) at least one buffering agent. Two or more buffering agents may be used in combination. Thus, a single type of buffering agent or a combination of different types of buffering agents may be used.

The buffering agent can stabilize the pH of the composition according to the present invention.

As the buffering agent, an amino acid, amino acid derivative, or a combination of an organic acid or inorganic acid and a salt thereof, are preferable, and an amino acid and amino acid derivative are more preferable, and an amino acid is even more preferable.

The amino acids that may be used are of natural or synthetic origin, in L, D or racemic form, and comprise at least one acid function chosen from carboxylic acid, sulfonic acid, phosphonic acid, and phosphoric acid functions. The amino acids may be in their neutral or ionic form.

As amino acids, mention, in a nonlimiting manner, may be made of glycine, aspartic acid, glutamic acid, alanine, arginine, ornithine, citrulline, asparagine, carnitine, cysteine, glutamine, lysine, histidine, lysine, isoleucine, leucine, methionine, N-phenylalanine, proline, serine, taurine, threonine, tryptophan, tyrosine, and valine. Glycine is more preferable, because glycine may also function to reduce skin staining.

As examples of the organic acid, mention may be made of lactic acid, citric acid and malic acid.

As examples of the salt, mention may be made of alkaline metal salts such as sodium salt, potassium salt, alkaline earth metal salt such as calcium salt, and ammonium salt.

The amount of the (c) buffering agent(s) in the composition according to the present invention may range from 0.1 to 15% by weight, preferably from 0.5 to 10% by weight, and more preferably from 0.5 to 5% by weight, relative to the total weight of the composition.

[Organic Solvent]

It is preferable that the composition according to the present invention further comprise (d) at least one organic solvent. Two or more organic solvents may be used in combination. Thus, a single type of organic solvent or a combination of different types of organic solvents may be used.

The organic solvent is preferably water miscible. As the organic solvent, there may be mentioned, for example, C$_1$-C$_4$ alkanols, such as ethanol and isopropanol; polyols and polyol ethers such as glycerol, 2-butoxyethanol, propylene glycol, monomethyl ether of propylene glycol, monoethyl ether and monomethyl ether of diethylene glycol; and aromatic alcohols such as benzyl alcohol and phenoxyethanol; analogous products; and mixtures thereof.

The amount of the (d) organic solvent(s) in the composition according to the present invention may range from 1 to 35% by weight, preferably from 5 to 25% by weight, and more preferably from 10 to 15% by weight, relative to the total weight of the composition.

[Other Ingredients]

The pH of the composition according to the present invention may be adjusted to the desired value using acidifying or basifying agents commonly used in dyeing keratinous fibers or else using conventional buffer systems.

Among the acidifying agents, mention may be made, by way of example, of mineral or organic acids such as hydrochloric acid, ortho-phosphoric acid, sulfuric acid, carboxylic acids such as acetic acid, tartaric acid, citric acid, and lactic acid, and sulfonic acids.

Among the basifying agents, mention may be made, by way of example, of ammonium hydroxide, alkali metal carbonates, alkanolamines such as mono-, di- and triethanolamines and also their derivatives, sodium or potassium hydroxide and compounds of the formula below:

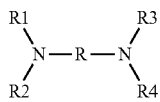

wherein

R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical or a $C_1$-$C_4$ hydroxyalkyl radical, which may be exemplified by 1,3-propanediamine and derivatives thereof. Sodium or potassium hydroxide is preferable, because this can also function to form in situ the (c) buffering agent.

The acidifying or basifying agent may be used in an amount ranging from 0.001 to 15% by weight, preferably from 0.01 to 10% by weight, and more preferably from 0.1 to 5% by weight, relative to the total weight of the composition.

The composition according to the present invention may comprise at least one thickening agent.

The thickening agent may be selected from organic and inorganic thickeners. The organic thickeners may be chosen from at least one of:
(i) associative thickeners;
(ii) crosslinked acrylic acid homopolymers;
(iii) crosslinked copolymers of (meth)acrylic acid and of ($C_1$-$C_6$)alkyl acrylate;
(iv) nonionic homopolymers and copolymers comprising at least one of ethylenically unsaturated ester monomers and ethylenically unsaturated amide monomers;
(v) ammonium acrylate homopolymers and copolymers of ammonium acrylate and of acrylamide;
(vi) polysaccharides such as cellulose and its derivatives; and
(vii) $C_{12}$-$C_{30}$ fatty alcohols.

The thickening agent is preferably selected from polysaccharides such as starch, xanthan gum, and hydroxyethylcellulose.

As used herein, the expression "associative thickener" means an amphiphilic thickener comprising both hydrophilic units and hydrophobic units, for example, comprising at least one $C_8$-$C_{30}$ fatty chain and at least one hydrophilic unit.

The viscosity of the composition according to the present invention is not particularly limited. The viscosity can be measured at 25° C. with viscosimeters or rheometers preferably with coneplan geometry. Preferably, the viscosity of the composition according to the present invention can range, for example, from 1 to 2000 Pa·s, and preferably from 1 to 1000 Pa·s at 25° C. and 1 $s^{-1}$.

The thickening agent may be present in an amount ranging from 0.001 to 10% by weight, and preferably from 0.01 to 10% by weight, such as from 0.1 to 5% by weight, relative to the total weight of the composition.

The compositions according to the present invention may also contain various adjuvants conventionally used in compositions for dyeing hair, such as anionic, non-ionic, cationic, amphoteric or zwitterionic polymers, or mixtures thereof, antioxidants, penetrating agents, sequestering agents, fragrances, dispersing agents, conditioning agents, film-forming agents, ceramides, preservatives and opacifying agents.

The form of the composition according to the present invention is not particularly limited, as long as it is water-based, and may take various forms such as an emulsion, an aqueous gel, an aqueous solution, or the like.

The composition according to the present invention is a composition for dyeing keratin fibers, and is preferably a cosmetic composition for dyeing keratin fibers. The "keratin fibers" here mean fibers which include at least one keratin substance. It is preferable that at least a part of the surface of the keratin fibers be formed by keratin fibers. Examples of keratin fibers include hair, eyebrows, eyelashes, and the like. It is preferable that the composition according to the present invention be used for dyeing hair.

[Preparation]

The composition according to the present invention can be prepared by mixing (a) at least one direct dye, and (b) at least one sulfone compound according to the above formula (I), as essential ingredients, as well as optional ingredient(s) as explained above.

The method and means to mix the above essential and optional ingredients are not limited. Any conventional method and means can be used to mix the above essential and optional ingredients to prepare the composition according to the present invention.

The composition according to the present invention is preferably a so-called one-part composition or a ready-to-use composition. For the purposes of the present invention, the expression "ready-to-use composition" is defined herein as a composition to be applied immediately to keratin fibers such as hair.

As compared to a so-called two-part composition, a so-called one-part composition does not need to mix ingredients in the composition prior to use. Therefore, it is easy for a consumer to use the composition according to the present invention for dyeing keratin fibers. Furthermore, stable coloring of keratin fibers is possible for the composition according to the present invention, because it is not possible to fail to mix ingredients in a precise mixing ratio which is required for two-part compositions for dyeing keratin fibers.

[Process]

The present invention also relates to a process for dyeing keratin fibers, comprising the step of applying the composition according to the present invention to the keratin fibers.

The step of applying the composition according to the present invention to the keratin fibers can be performed by a conventional applicator such as a brush, or even by the hands.

The keratin fibers to which the composition according to the present invention has been applied can be left for an appropriate time which is required to treat the keratin fibers. The time length for the treatment is not limited, but it may be from 1 minute to 1 hour, preferably 1 minute to 30 minutes, and more preferably 1 minute to 15 minutes. For example, the time for dyeing the keratin fibers may be from 1 to 20 minutes, preferably 5 to 15 minutes.

The keratin fibers may be treated at room temperature. Alternatively, the keratin fibers can be heated at 25° C. to 65° C., preferably 30° C. to 60° C., more preferably 35° C. to 55° C., and even more preferably 40° C. to 50° C., during the step of applying the composition according to the present invention to the keratin fibers, and/or the step of leaving the keratin fibers to which the composition according to the present invention has been applied.

The keratin fibers may be rinsed after the step of applying the composition according to the keratin fibers onto the keratin fibers and/or after the step of leaving the keratin fibers to which the composition according to the present invention has been applied.

The present invention may also relate to the use of the composition according to the present invention for dyeing keratin fibers such as hair.

EXAMPLES

The present invention will be described in a more detailed manner by way of examples. However, these examples should not be construed as limiting the scope of the present invention.

Examples 1-7 and Comparative Examples 1-2

[Preparation]

Each of the cosmetic compositions for dyeing hair according to Examples 1-7 (Ex. 1 to Ex. 7) and Comparative Examples 1-2 (Comp. Ex. 1 and Comp. Ex. 2) was prepared by mixing the ingredients shown in Table 1 at room temperature, and were poured into transparent vessels with the same volume. The numerical values for the amounts of the ingredients are all based on "% by weight" as active raw materials.

[Evaluation of Color Difference]

Each of the compositions according to Examples 1-7 and Comparative Examples 1-2 was evenly applied onto 1 g of a tress of 90% gray natural human hair. The tress was then left for 15 minutes at 40° C., followed by washing with water, shampooing, rinsing once and drying the tress. The difference in color of the tress before and after the above dyeing process was evaluated by using Minolta CM-580. ΔE* (between the color of the undyed original tress and the color of the dyed tress based on CIE1976) was calculated. Evaluation of the color difference was carried out in accordance with the following criteria.

A: ΔE* value is greater than 25

B: ΔE* value is between 20 and 25

C: ΔE* value is below 20

The larger ΔE* is, the better the dyeing is. The results are shown in Table 1.

[Evaluation of Skin Staining]

The skin staining of the composition was subjected to the sensory evaluation by 10 experts. Each of the compositions according to Examples 1-7 and Comparative Examples 1-2 was applied onto the surface of a forearm of 10 human experts. The applied surface was left for 15 minutes at room temperature, followed by thoroughly washing out the composition with water, and drying the surface. Evaluation was carried out in accordance with the following criteria.

A: At least 80% of 10 experts recognized skin staining to be absolutely unnoticeable.

B: At least 50% but less than 80% of 10 experts recognized skin staining to be absolutely unnoticeable.

C: At least 20% but less than 50% of 10 experts recognized skin staining to be absolutely unnoticeable.

D: Less than 20% of 10 experts recognized skin staining to be absolutely unnoticeable.

The results are shown in Table 1.

TABLE 1

|  | Ex. 1 | Ex. 2 | Ex. 3 | Ex. 4 | Ex. 5 | Ex. 6 | Ex. 7 | Comp. Ex. 1 | Comp. Ex. 2 |
| --- | --- | --- | --- | --- | --- | --- | --- | --- | --- |
| Hydroxyethylcellulose | 1.5 | 1.5 | 1.5 | 1.5 | 1.5 | 1.5 | 1.5 | 1.5 | 1.5 |
| Phenoxyethanol | 0.5 | 0.5 | 0.5 | 0.5 | 0.5 | 0.5 | 0.5 | 0.5 | 0.5 |
| Ethanol | 12 | 12 | 12 | 12 | 12 | 12 | 12 | 12 | 12 |
| Propyleneglycol | 1 | 1 | 1 | 1 | 1 | 1 | 1 | 1 | 1 |
| Lactic acid | 2 | 2 | 2 | 2 | 2 | 2 | 2 | 2 | 2 |
| Sodium hydroxide | qs pH3 | qs pH3 | qs pH3 | qs pH3 | qs pH3 | qs pH3 | qs pH3 | qs pH3 | qs pH3 |
| Yellow 5 | 0.115 | 0.115 | 0.115 | 0.115 | 0.115 | 0.115 | 0.115 | 0.115 | 0.115 |
| Orange 4 | 0.13 | 0.13 | 0.13 | 0.13 | 0.13 | 0.13 | 0.13 | 0.13 | 0.13 |
| EXT. Violet 2 | 0.07 | 0.07 | 0.07 | 0.07 | 0.07 | 0.07 | 0.07 | 0.07 | 0.07 |
| Acid Black 1 | 0.015 | 0.015 | 0.015 | 0.015 | 0.015 | 0.015 | 0.015 | 0.015 | 0.015 |
| Glycine | — | — | 1 | — | — | — | — | — | 1 |
| Dimethylsulfone | 2 | 4 | 4 | 8 | — | — | — | — | — |
| Sulfonane | — | — | — | — | 4 | — | — | — | — |
| Diphenylsulfone | — | — | — | — | — | 4 | — | — | — |
| Ethylmethylsulfone | — | — | — | — | — | — | 4 | — | — |
| Water | qs 100 | qs 100 | qs 100 | qs 100 | qs 100 | qs 100 | qs 100 | qs 100 | qs 100 |
| ΔE* | B | B | A | B | B | A | A | B | B |
| Skin Staining | B | A | A | A | A | A | A | D | C |

It can be recognized from the experimental results shown in Table 1 that when a cosmetic composition for dyeing hair containing a direct dye further contains a sulfone compound, the cosmetic composition can prevent or reduce skin staining by the direct dye on the skin such as the scalp, while maintaining good cosmetic effects such as good coloring properties.

The invention claimed is:

1. A composition for dyeing keratin fibers, comprising:
   (a) at least one direct dye;
   (b) at least one sulfone compound corresponding to formula (I) below:

(I)

wherein:
   each of $R^1$ and $R^2$ independently denotes a monovalent $C_{1-30}$ aliphatic group or a monovalent $C_{6-30}$ aromatic group, which may optionally be substituted with at least one substituent; or
   $R^1$ and $R^2$, together with the sulfur atom which they are bonded to, form a 3-10 membered ring which may optionally be substituted with at least one substituent; and
   (c) at least one organic solvent.

2. The composition according to claim 1, wherein the at least one direct dye is chosen from acidic direct dyes, basic direct dyes, or neutral direct dyes.

3. The composition according to claim 1, wherein the at least one direct dye is selected from:
the diaryl anionic azo dyes corresponding to formula (II) or (II') below:

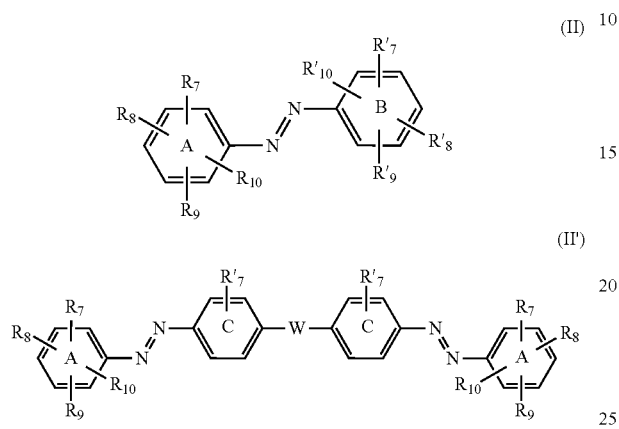

wherein:
R$_7$, R$_8$, R$_9$, R$_{10}$, R'$_7$, R'$_9$ and R'$_{10}$, which may be identical or different, are chosen from a hydrogen atom or a group chosen from:
alkyl;
alkoxy or alkylthio;
hydroxyl or mercapto;
nitro;
R°—C(X)—X'—, R°—X'—C(X)—, or R°—X'—C(X)—X"— wherein R° is chosen from a hydrogen atom, alkyl group, or aryl group; X, X', and X", which may be identical or different, are chosen from an oxygen or sulfur atom, or NR wherein R is chosen from a hydrogen atom or an alkyl group;
(O)$_2$S(O$^-$)—, X$^+$ wherein X$^+$ is chosen from an organic or mineral cationic counter ion;
(O)CO$^-$— or X$^+$;
(O)P(O$_2^-$)— or 2X$^+$;
R"—S(O)$_2$—, wherein R" is chosen from a hydrogen atom, alkyl group, aryl group, (di)(alkyl)amino group, aryl(alkyl)amino group, phenylamino group, or phenyl group;
R'''—S(O)$_2$—X'— wherein R''' is chosen from an alkyl or optionally substituted aryl group;
(di)(alkyl)amino;
aryl(alkyl)amino optionally substituted with at least one group chosen from nitro, nitroso, (O)$_2$S(O$^-$)—, X$^+$, or alkoxy with X$^+$;
optionally substituted heteroaryl; benzothiazolyl group;
cycloalkyl;
cyclohexyl;
Ar—N═N— wherein Ar is chosen from an optionally substituted aryl group, a phenyl optionally substituted with at least one alkyl, (O)$_2$S(O$^-$)—, X$^+$, or phenylamino groups;
or alternatively two contiguous groups R$_7$ with R$_8$, R$_8$ with R$_9$, or R$_9$ with R$_{10}$, together form a fused benzo group A'; and R'$_7$ with R'$_8$ or R'$_8$ with R'$_9$ or R'$_9$ with R'$_{10}$ together form a fused benzo group B'; wherein A' and B' are optionally substituted with at least one group chosen from nitro, nitroso, (O)$_2$S(O$^-$)—, X$^+$, hydroxyl, mercapto, (di)(alkyl)amino, R°—C(X)—X', R°—X'—C(X)—, R°—X'—C(X)—X"—, Ar—N═N—, or optionally substituted aryl(alkyl) amino;

W is chosen from a sigma bond a, an oxygen or sulfur atom, or a divalent radical —NR—, or methylene —C(R$_a$)(R$_b$)—, wherein R$_a$ and R$_b$, which may be identical or different, are chosen from a hydrogen atom or an aryl group, or alternatively R$_a$ and R$_b$ form, together with the carbon atom that bears them, a spiro cycloalkyl;

wherein formulae (II) and (II') comprise at least one sulfonate (O)$_2$S(O$^-$)—, X$^+$, phosphonate (O)P(O$_2^-$) 2X$^+$, or carboxylate (O)C(O$^-$)—, X$^+$ radical on one of the rings A, A', B, B' or C;

the anthraquinone dyes corresponding to formula (III) or (III') below:

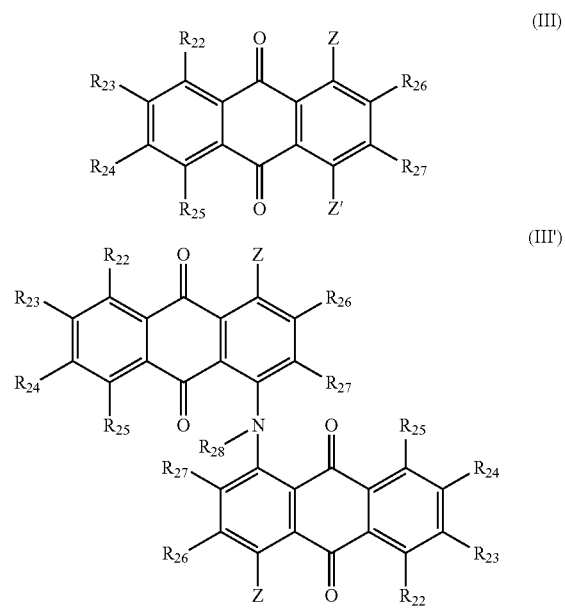

wherein:
R$_{22}$, R$_{23}$, R$_{24}$, R$_{25}$, R$_{26}$ and R$_{27}$, which may be identical or different, represent a hydrogen or halogen atom or a group chosen from:
alkyl;
hydroxyl or mercapto;
alkoxy or alkylthio;
aryloxy or arylthio optionally substituted, preferably substituted with one or more groups chosen from alkyl and (O)$_2$S(O$^-$)—, X$^+$ with X$^+$ representing an organic or mineral cationic counter ion;
aryl(alkyl)amino optionally substituted with one or more groups chosen from alkyl and (O)$_2$S(O$^-$)—, X$^+$;
(di)(alkyl)amino;
(di)(hydroxyalkyl)amino;
(O)$_2$S(O$^-$)— or X$^+$;
Z' is chosen from a hydrogen atom or a NR$_{28}$R$_{29}$ group, wherein R$_{28}$ and R$_{29}$, which may be identical or different, are chosen from a hydrogen atom or a group chosen from:

alkyl;
polyhydroxyalkyl or hydroxyethyl;
aryl optionally substituted with at least one group chosen from alkyl, methyl, n-dodecyl, n-butyl, $(O)_2S(O^-)—$, $X^+$, $R°—C(X)—X'—$, $R°—X'—C(X)—$, $R°—X'—C(X)—X''—$; or
cycloakyl or cyclohexyl; and Z is chosen from a hydroxyl group or $NR'_{28}R'_{29}$, wherein $R'_{28}$ and $R'_{29}$, which may be identical or different, are chosen from a hydrogen atom or a group chosen from:
alkyl;
polyhydroxyalkyl or hydroxyethyl;
aryl optionally substituted with at least one group chosen from alkyl, methyl, n-dodecyl, n-butyl, $(O)_2S(O^-)—$, $X^+$, $R°—C(X)—X'—$, $R°—X'—C(X)—$, $R°—X'—C(X)—X''—$; or
cycloakyl or cyclohexyl;

wherein formulae (III) and (III') comprise at least one sulfonate group $(O)_2S(O^-)—$, $X^+$; or the quinoline-based dyes corresponding to formula (IV) below:

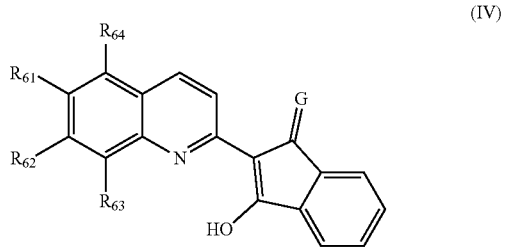

wherein:
$R_{61}$ is chosen from a hydrogen, halogen atom or an alkyl group;
$R_{62}$, $R_{63}$ and $R_{64}$, which may be identical or different, are chosen from a hydrogen atom or a $(O)_2S(O^-)—$, $X^+$ group, wherein $X^+$ is chosen from an organic or mineral cationic counter ion;
or alternatively $R_{61}$ with $R_{62}$, or $R_{61}$ with $R_{64}$, together form a benzo group optionally substituted with at least one $(O)_2S(O^-)—$, $X^+$ group; and
G is chosen from an oxygen or sulfur atom or a $NR_e$ group, wherein $R_e$ is chosen from a hydrogen atom or an alkyl group;
wherein formula (IV) comprises at least one $(O)_2S(O^-)—$, $X^+$ group.

4. The composition according to claim 1, wherein the at least one direct dye is present in an amount ranging from about 0.001% to about 5% by weight, relative to the total weight of the composition.

5. The composition according to claim 1, wherein the at least one direct dye is present in an amount ranging from about 0.05% to about 2% by weight, relative to the total weight of the composition.

6. The composition according to claim 1, wherein the monovalent $C_{1-30}$ aliphatic group is chosen from a saturated monovalent $C_{1-30}$ aliphatic hydrocarbon group, a linear or branched $C_{1-30}$ alkyl group, a $C_{3-30}$ cycloalkyl group, or an unsaturated monovalent $C_{2-30}$ aliphatic hydrocarbon group.

7. The composition according to claim 1, wherein the monovalent $C_{6-30}$ aromatic group is a monovalent $C_{6-30}$ aromatic hydrocarbon group.

8. The composition according to claim 7, wherein the monovalent $C_{6-30}$ aromatic hydrocarbon group is a $C_{6-30}$ aryl group, or a linear or branched $C_{7-30}$ aralkyl group.

9. The composition according to claim 1, wherein $R^1$ and $R^2$, together with the sulfur atom which they are bonded to, form a 3-10 membered aliphatic ring which may optionally be substituted with at least one substituent.

10. The composition according to claim 1, wherein the at least one sulfone compound is present in an amount ranging from about 0.5% to about 30% by weight, relative to the total weight of the composition.

11. The composition according to claim 1, wherein the at least one sulfone compound is present in an amount ranging from about 2% to about 10% by weight, relative to the total weight of the composition.

12. The composition according to claim 1, further comprising water.

13. The composition according to claim 1, wherein the pH of the composition ranges from about 2 to about 7.

14. The composition according to claim 1, further comprising at least one buffering agent chosen from an amino acid, amino acid derivative, a combination of an organic acid or inorganic acid, or salt thereof.

15. The composition according to claim 14, wherein the at least one buffering agent is present in an amount ranging from about 0.1% to about 15% by weight, relative to the total weight of the composition.

16. The composition according to claim 14, wherein the at least one buffering agent is present in an amount ranging from about 0.5% to about 5% by weight, relative to the total weight of the composition.

17. The composition according to claim 1, wherein the at least one organic solvent is present in an amount ranging from about 1 to about 35% by weight, relative to the total weight of the composition.

18. The composition according to claim 1, wherein the at least one organic solvent is present in an amount ranging from about 10% to about 15% by weight, relative to the total weight of the composition.

* * * * *

UNITED STATES PATENT AND TRADEMARK OFFICE
CERTIFICATE OF CORRECTION

PATENT NO.         : 10,292,920 B2
APPLICATION NO.    : 15/315512
DATED              : May 21, 2019
INVENTOR(S)        : Shiho Miyake et al.

It is certified that error appears in the above-identified patent and that said Letters Patent is hereby corrected as shown below:

In the Claims

Column 20, Line 7, after "bond" please change "a" to -- σ --.

Signed and Sealed this
Ninth Day of July, 2019

Andrei Iancu
*Director of the United States Patent and Trademark Office*